United States Patent [19]
Osmanski

[11] Patent Number: 5,710,373
[45] Date of Patent: Jan. 20, 1998

[54] VISUAL COMPARATOR WITH TEST CHART AND METHOD FOR EVALUATING CONTAMINATION OF WASHING FLUIDS

[75] Inventor: Frank A. Osmanski, Hanover Park, Ill.

[73] Assignee: Safety-Kleen Corporation, Elgin, Ill.

[21] Appl. No.: 800,597

[22] Filed: Feb. 18, 1997

[51] Int. Cl.⁶ .......................... G01N 33/28; G01N 21/71; G01N 15/07; G01D 21/00
[52] U.S. Cl. .................... 73/53.05; 73/53.07; 73/61.71; 73/53.03
[58] Field of Search ..................... 73/53.01, 53.02, 73/53.05, 53.03, 53.07, 61.71, 54.03

[56] References Cited

U.S. PATENT DOCUMENTS

| | | | |
|---|---|---|---|
| 2,016,832 | 10/1935 | Hyatt et al. | 88/14 |
| 2,062,929 | 12/1936 | Powers | 88/14 |
| 3,003,353 | 10/1961 | Swadesh | 73/73 |
| 3,408,860 | 11/1968 | Knieriem et al. | 73/73 |
| 4,448,887 | 5/1984 | Kauffman et al. | 436/60 |
| 4,779,451 | 10/1988 | Ezawa et al. | 73/53 |
| 5,132,225 | 7/1992 | Dickakian et al. | 436/60 |
| 5,194,910 | 3/1993 | Kirkpatrick, Jr. | 356/70 |
| 5,200,064 | 4/1993 | Russ et al. | 210/94 |
| 5,244,586 | 9/1993 | Hawkins et al. | 210/806 |
| 5,313,824 | 5/1994 | Herguth et al. | 73/53.05 |

Primary Examiner—Hezron E. Williams
Assistant Examiner—J. David Wiggins
Attorney, Agent, or Firm—James T. FitzGibbon

[57] ABSTRACT

A visual comparator for use in evaluating the nature and extent of contamination in a solvent used for cleaning mechanical parts. The comparator comprises an opaque frame, and an array of viewing apertures is formed in the frame. Each of said apertures is covered by a translucent viewing panel, with certain of the viewing panels comprising a first array having a graduated sequence of predetermined colors and optical densities, each indicative of a given level of soluble liquid contamination. The remainder of the viewing panels comprises a second array having a graduated sequence of graduated optical densities, each indicative of a given level of contamination by suspended particles. The arrays are arranged so as to facilitate comparison between both the color and optical density of a sample of solvent received in a transparent tube, and both the color and optical density of a particular viewing panel when said viewing panel and said sample-containing tube are illuminated by an intense but diffused light source.

12 Claims, 1 Drawing Sheet

U.S. Patent    Jan. 20, 1998    5,710,373
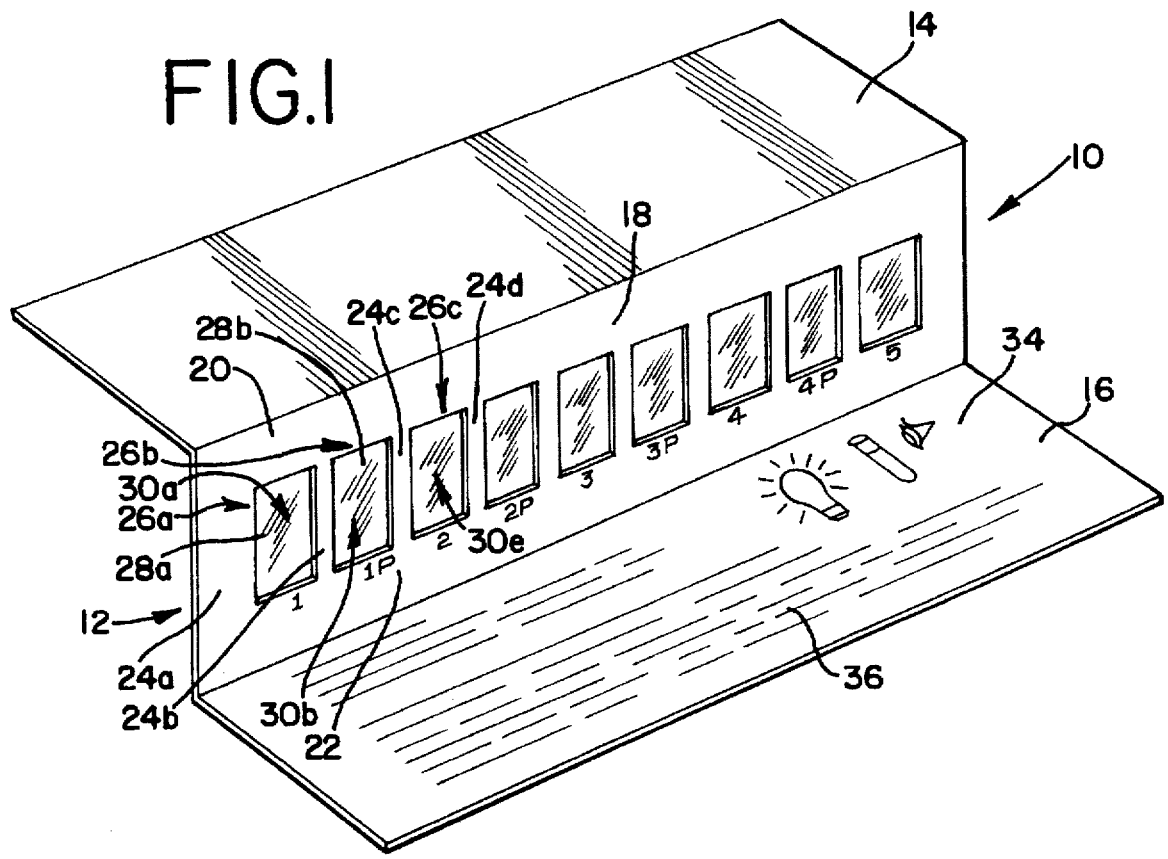
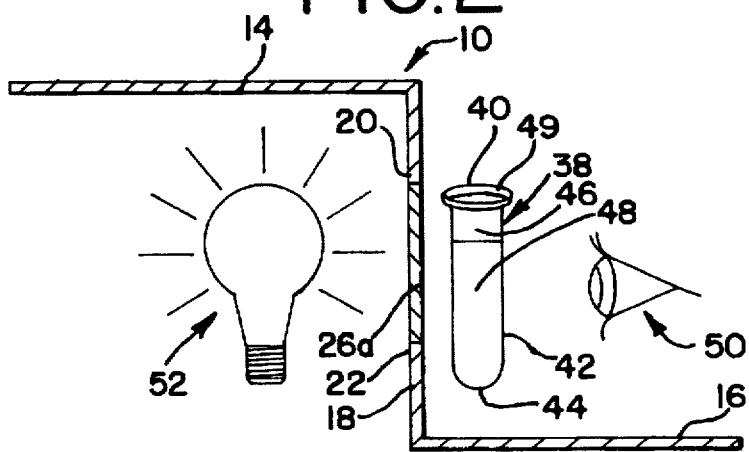

VISUAL COMPARATOR WITH TEST CHART AND METHOD FOR EVALUATING CONTAMINATION OF WASHING FLUIDS

BACKGROUND OF THE INVENTION

The present invention relates generally to multi-function test charts and like apparatus and more particularly, to a low cost, readily portable test kit, including a chart arranged to permit examination of the nature and extent to which a charge of parts washing solvent or similar fluid contained in a reservoir is contaminated. In addition, the invention relates to methods of using a test kit and, where indicated, treating solvent with a clarifying agent, thereby permitting a user to avoid or delay recycling a fluid, such as contaminated parts washing solvent, until such recycling is actually needed.

In recent years, apparatus and methods used to wash mechanical parts as an incident to maintenance and repair of machines of all kinds have progressed from the highly rudimentary, gasoline-in-the-pan approach to a safer and more sophisticated operation wherein equipment designed specifically for parts washing has become very popular throughout the United States and foreign countries. U.S. Pat. No. 3,522,814 described the first parts washer which was instrumental in establishing parts washing as an independent industry, and in particular, described a parts washer that would change the practice of parts washing from a hit-or-miss proposition to a full fledged service operation. Using this equipment, mechanics and others could ensure themselves that parts were being cleaned with maximum effectiveness and that hazards such as fire, spillage, and the like were minimized.

Shortly after the invention and development of the parts washer described in the above patent, awareness of other difficulties with prior solvent cleaning methods were discovered. Government regulations, such as OSHA regulations, created a demand for the use of solvent which was relatively safe for use in the workplace and, in addition to providing safety against the hazards of fire and an explosion, such solvent was formulated to minimize evaporation and possible damage due to inhalation of vapors and related risks.

Still later, as awareness of the need to minimize contamination became more apparent, attention was directed to more effective methods of recycling. In this connection, the use of parts washers of the above-described kind, commonly referred to as the first parts washer that could be serviced by one man in one minute, enabled efforts to be concentrated on efficient, low-cost recycling.

At the present time, when the need for and fact of solvent recycling are well established as an industry, the concept of so-called waste minimization has emerged as an important aspect or sub-set of recycling, particularly as it affects industrial operations. According to the concept of waste minimization, recycling operations, which implicitly involve separating and discarding certain contaminants while recycling the remainder of contaminated feedstock, can be affected by any given user's decision to initiate recycling at a particular time.

Where the recycling function is attended to as a part of a service, such as periodically replacing an entire batch of solvent, the decision of when to initiate the process is one that should be made using the best available criteria. Regarding parts washing solvent, the solvent as initially furnished to the customer is quite effective to clean dirty, grease-and-oil encrusted parts. As the cleaning cycle progresses, the solvent absorbs those miscible contaminants which include oils, anti-freeze or the oily components of greases and the like, that are truly soluble in the parts washing solvent. Eventually, these will attain a concentration sufficient to compromise the cleaning effectiveness of the solvent. If the parts being washed do not dry rapidly, or contain an oil film which is undesirable for post-cleaning operations, little or no post-cleaning film is permitted. In other cases, a slight residue is permissible.

However, in many cases, long before the parts washing solvent is highly contaminated by soluble oils and other such materials, the solvent begins to appear dirty as fine particulates become more or less permanently suspended therein. Thus, fine particles of carbon black, and dust and dirt particles of various kinds, become suspended in the solvent upon the agitation incident to the scrubbing and washing process, thereby giving the solvent a relatively opaque appearance. Although causing the user to believe instinctively that the solvent has exhausted its cleaning capability, this conclusion may be misleading, in that the suspended particles may in fact not compromise the ability of the product to clean mechanical parts.

In this connection, reference is made to U.S. patent application Ser. No. 08/678,467 ("'467"), filed Jul. 3, 1996, which is a continuation of application Ser. No. 08/271,847 ("'847"), filed Jul. 7, 1994, and now abandoned, which describe compositions and methods for accelerating the settlement of such finely dispersed particles within a mass of solvent so as to extend its service life.

According to the present invention, if the nature and extent of contaminants present in a cleaning solvent can be determined with relatively great accuracy, then waste incident to the recycling process can be minimized. Thus, every user desires not to pay for unnecessary replacement and/or replenishment of solvent and recycling of used solvent; however, the same user does not wish to use solvent beyond the point at which it is most effective, considering his own standards.

The effective end point of use may be different in certain applications, depending upon the tolerance for dissolved oil or other lubricants in the solvent. However, for the service representative to engage in an informed dialog with the user, the ability to analyze both the nature and extent of such contaminants is very important. Ideally, solvent contaminated with particulates but not with soluble constituents can be analyzed, treated, re-used and then re-analyzed, in some cases being treated several times; the test chart of the present invention facilitates this method.

In view of the need for discriminating among different forms of contamination and determining the extent to which contaminants are present in any given solvent, it is an object of the invention to provide an improved comparator-type solvent test chart.

Another object of the invention is to provide a solvent test or comparator chart which is simple and easy to use and which may be shown to a service station proprietor, machine repairman, or other solvent user and which is relatively self-explanatory in character.

Yet another object of the invention is to provide a comparator which includes plural apertures arranged in a definite sequence and able to be positioned relative to a light source and the eye of a technician so as to facilitate and simplify accurate comparison between predetermined standards embodying known levels of solvent contamination and an unknown solvent being analyzed.

Still another object of the invention is to provide a test chart or comparator which is reliable in use, is economical to manufacture, and durable enough to be susceptible of plural uses before being discarded.

A further object of the invention is to provide a comparator that will enable the service representative to render informed advice to a solvent user regarding the actual need for recycling the cleaning solvent.

A still further object of the invention is to provide a simple and inexpensive apparatus for use by service personnel in a waste minimization effort directed to users of parts washing or other commercial solvents.

Yet another object of the invention is to provide a method of solvent condition analysis and treatment which includes the steps of analyzing previously used solvent with the aid of a comparator-type test chart having plural apertures with viewing panels indicative of the character and quality of contaminants in the solvent, using such chart to determine whether the condition presented by the solvent may be remedied; applying a clarifying additive to the solvent; thereafter using the solvent and subsequently retesting it to determine whether it may again be reused without recycling; and repeating the observation and treatment steps periodically so as to determine an end point at which solvent recycling has become mandatory.

The foregoing and other objects and advantages of the invention are achieved in practice by providing a comparator chart with an opaque frame, an array of apertures formed in the frame with each aperture including a transparent or translucent insert having a pre-ordained color and optical density indicative of the extent of contamination by soluble materials, and an additional array of inserts showing varying levels of dissolved contaminants, with such films being arranged in a desired sequence to facilitate comparison, and with the entire comparator chart being arranged for presentation to a light source for side-by-side comparison of the levels of the solvent being tested.

The invention also achieves its objects by providing a method which includes observing the nature and extent of contamination of a used parts washing solvent, adding a clarifying additive to solvent contaminated with a high concentration of dispersed particulates, reusing the clarified solvent, and subsequently repeating the observations to determine whether additional treatment or recycling is desirable.

The exact manner in which the foregoing and other objects and advantages of the invention are achieved in practice will become more clearly apparent when reference is made to the following detailed description of the preferred embodiments of the invention set forth by way of example and shown in the accompanying drawings wherein like reference numbers indicate corresponding parts throughout.

BRIEF DESCRIPTIONS OF THE DRAWINGS

FIG. 1 is a perspective view of a comparator-type solvent test chart made in keeping with the invention;

FIG. 2 is a partly diagrammatic side view, partly in elevation and partly in section, showing the use of a preferred form of the solvent comparator chart of the invention.

DESCRIPTION OF THE PREFERRED EMBODIMENTS OF THE INVENTION

While it will be understood that the invention may be embodied in various forms and may be practiced by methods which vary somewhat from the forms illustrated, a representative embodiment of the invention will be described which represents the presently best and most convenient way of economically practicing the invention.

Referring now to the drawings in greater detail, FIG. 1 shows the invention to be embodied in a comparator-type test chart generally designated 10 and shown to include a frame generally designated 12, upper and lower flaps, 14, 16, and a center section 18. The center section 18 includes upper and lower marginal strips 20, 22, which, when combined with vertical marginal strips 24a, 24b, 24c, etc. serve to define a plurality of individual apertures generally designated 26a, 26b, 26c, etc.

The apertures 26a, 26b, etc. are arranged in a horizontal, left-to-right array. The marginal strips, such as the strips 20, 22, 24a, 24b defining a particular aperture 26a, for example, engage counterpart margins (not shown) of a translucent film 28a serving to define a viewing panel generally designated 30a. Similar viewing panels generally designated 30b, 30c, etc. are formed by sections of film material 28b, 28c having their outer margins embedded within or covered by the horizontal and vertical marginal strips defining each aperture.

In the preferred form, each viewing panel 30a, 30b, etc. includes a designation beneath it that indicates the intensity of contamination, and whether or not particulates are present. Thus, the viewing panels 30a, etc. or windows are labeled (from left to right) as 1, 1P, 2, 2P, 3, 3P, 4, 4P and 5, respectively. The number alone indicates the relative concentration of soluble contaminant, and the "P" suffix means that a particulate concentration is also present, in the relative concentration indicated by the number. FIG. 1 shows these legends.

Referring again to FIG. 1, it will be noted that, in the preferred form, the lower flap 16 includes a graphics display instructional area 34 and a written text instructional area 36 describing the preferred manner of performing tests using the inventive comparator chart 10.

Referring now to FIG. 2, there is shown a specimen holder in the form of a vial generally designated 38 having an open top 40 and transparent side and bottom walls 42, 44 defining an interior space 46 which in use is filled with a test liquid 48 and enclosed by a cover 49. When the eye of a user, schematically illustrated at 50, is positioned such that the tube or vial 38, a selected aperture 26a, and a light source generally designated 52 are all aligned, the user may make a visual comparison between the film in one of the viewing apertures (representing a given standard) and the vial 38 containing a solvent specimen 48. The vial is moved among the apertures and aligned to secure the closest possible match of color and opacity.

According to the invention, the method may be practiced in at least two ways, as will now be discussed. As referred to above in the specification, whether a cleaning solvent has retained its ability to continue cleaning effectively depends on its condition. Specifically, its cleaning ability may be compromised by either an excess concentration of soluble materials, or an excess concentration of particulate materials, or both. On the other hand, the solvent may have an appearance of being contaminated, but such appearance may be the result of a "false positive" indicating the presence of enough particulate contamination to imply that cleaning action has been impaired.

Thus, it is possible for solvent, which contains a high concentration of finely dispersed, suspended particles, to be treated by the addition of a so-called clarifying agent. This will cause these particles to coalesce or agglomerate, and settle into a portion of the liquid solvent near the bottom of its container.

Such materials are described and claimed in the "'467" and "'847" patent applications referred to above. Various materials (among those listed in the above application) that are effective to reduce particulate concentration in a supernatant layer of liquid preferably include ethylhexane diol ("EHD"), specifically 2-ethyl 1,3-hexane diol. Other materials include diethylene glycol mono-butyl ether ("DEGBE") and propylene glycol n-butyl ether ("PnBE"). In other instances, a combination of the EHD and the above or other so-called glycol ethers may be effective. Also, in certain instances, a few drops of water (up to an amount equal to the amount of clarifying agent) may be added to the treatment mix in order to affect the rate of settling. Generally speaking, such clarifying agents are mixed with the solvent in amount of 0.5 up to 5 parts per hundred ("pph") of solvent, usually about 1 or 2 pph.

Collectively speaking, and without regard to which particular composition or mixture of composition may prove most effective for this purpose, (which is beyond the scope of the present invention,) such materials will be referred to herein and in the claims simply as "clarifying agents". The method of the invention does not depend on the exact composition of the clarifying agent.

Referring again to one method of practicing the invention, a service representative, preferably in the presence of a user of solvent, actuates the pump portion of a parts washer of the type shown in the above referenced U.S. Pat. No. 3,522,814, causing solvent to flow from the output nozzle, and captures a specimen of solvent in a tube or vial 38 which is filled to a suitable level such as that shown in FIG. 2.

According to the invention, the first aperture 26a includes a viewing panel 30a which is a comparatively light, yellow/brown color and is identified by the number "1". This is the color of a slightly oily solvent. The second viewing panel 30b is made to represent the color and translucency of a solvent having the same concentration of soluble oils as that shown in panel 30a, but also includes a darker, generally gray colored component indicative of a definite level of particulates. This bears the legend "1P". Each alternate viewing panel, namely the third, fifth, seventh and ninth panels respectively designated 30c, 30e, 30g and 30i is given a number, i.e., 2, 3, 4 and 5, and each is progressively darker on the yellow/brown scale. The series represents a progressively increasing concentration of typical soluble oils or the like. The panel 30i is virtually opaque and the panel 30g is a dark, slightly translucent panel of a relatively dark brown color.

Regarding the four alternate viewing panels, namely panels 30b, 30d, 30f, and 30h; these bear the legends 1P, 2P, 3P and 4P, respectively. Each of these includes the coloration attributable to the soluble oil of its counterpart 30a, 30c, etc. (add numbered panels) but each further includes a gradually darkening grayish-black color representative of a gradually increasing concentration of dispersed particulates. The overall color of each of the numbered or "P" panels 30b, 30d, etc. is progressively more gray and is a color which is best described as being the same hue as that of the preceding viewing panel, only with an additional black or gray component attributable to the presence of fine particles.

A preferred form of chart contains the following "Contamination Guidelines":

| CONTAMINATION GUIDELINES | |
|---|---|
| 1 - 2 - 3 | Probable light to medium oil contamination. Minimal suspended particles. |
| 1P - 2P - 3P | Suspended particles visible, causing some significant color darkening |
| 4 | Probable high oil contamination. No visible suspended particles. |
| 4P | Suspended particles present. |
| 5 | Solvent totally opaque. High particle contamination probable. |

Referring again to the method, after the specimen holder or vial 38 has been held up next to each of a succession of viewing panels for comparison purposes, it is possible to determine which of the panels the specimen most clearly matches. From this point, a determination is made as to the steps to be taken. If the specimen matches panels 1 or 2, or sometimes 3, no action is indicated, especially if the application will tolerate a certain percentage of dissolved oils. The same may be true for panel 1P in some cases. If the vial matches specimen panels 2P or 3P, (and in some cases 1P), then adding the clarifying agent is suggested.

If so, an addition of perhaps 2 or 3 pph of clarifying agents is carried out. The solvent is then placed into use and such use is continued for a given period. This usually approximates the prior time between initial furnishing of new or reconditioned solvent and detecting the need for clarification. After testing, the solvent is re-clarified, if possible. This may occur two or three times before further clarification cannot be achieved. After the test chart 10 has been used for comparison purposes as just described, it may be stored for further use by folding the flaps so that the lower flap 16 folds upwardly and covers the front surface of the center section 18, and the upper flap 14 folds downwardly to cover the rear surface of the center section 18, thereby comprising protective covers for the viewing panel portions of the test chart 10.

Thus, in its simplest form, the method comprises testing the solvent using the chart of the invention and adding the clarifying agent when indicated or desired.

A second aspect of the method is similar, except that the clarification effectiveness can be evaluated within a short time. Thus, assuming that clarification is indicated, as by having the specimen vial match panels 3P or 4P, for example, then the clarifying agent is added in the above-referenced proportions and a short time, such as 15 minutes to one hour is allowed to elapse. Depending on the liquid level from which the specimen is taken, clarification may be readily apparent within the matter of several minutes to an hour or less.

If this treatment is indicated and proves effective, then the solvent is reused and additions are made periodically, following by, testing so as to obtain a before- and after-comparison of solvent clarity. When clarification is not able to be achieved after about one or two hours, for example, after addition of clarifying agent, it may be assumed that further agglomeration and settling of dispersed particles cannot be achieved. Thereupon, the solvent is identified as being in need of recycling and service personnel may pick up the contaminated solvent and replace it with new solvent to initiate a following cycle or series of test-and-clean cycles.

If, in carrying out either of the just-described methods, the degree of soluble contaminants becomes excessive, i.e., for example, no substantial amounts of particulates are visible, but the dissolved oils show a color intensity equal to that of viewing panels identified by the legends or 4 or 5, then recycling is suggested regardless of the addition of clarifying agents. This method may be summarized as including the steps of using solvent, testing it for both sorts of contaminants, clarifying the solvent while soluble contaminants are at or below an acceptable level, repeating the clarifying steps as long as these steps are effective and provided that soluble contaminants are not present in excess proportions, and then recycling the solvent when one or both of the soluble/insoluble contaminants level criteria cannot be met.

The preferred form of test chart is simply made from paper with a transparent photographic or similar film used to provide the viewing panels. The detailed instructions are shown as preferably being illustrated and described in one of the panels forming a part of the test chart for convenience and simplicity. The arrangement has been shown as alternating between solvent and particulate contamination, i.e., viewing panels are arranged as 1, 1P, 2, 2P, etc. However, another arrangement such as the 1, 2, 3, 4, and on one side of the chart and a 1P, 2P, etc. arrangement on another portion of the chart is considered to fall within the inventive concept if such arrangement proves practical.

It is believed that prior test charts are known wherein the degree to which a lubricating oil is contaminated may be determined by comparison with reference panels. However, the present invention enables a solvent material to be analyzed for two distinct kinds of contaminants, some of which may compromise its effectiveness and others which may not, and hence, the invention makes it possible to discriminate among such types of contaminants and also to remedy curable difficulties while not overlooking contamination that in fact does require recycling, all in the interest of waste minimization and cost reduction.

It will thus be seen that the present invention provides a novel apparatus and method having a number of advantages and characteristics including those pointed out herein and others which are inherent in the invention. A preferred embodiment having been described in detail by way of example, it is apparent that variations and modifications to the described form of apparatus and methods may be made without departing from the spirit of the invention or the scope of the appended claims.

I claim:

1. A visual comparator for use in evaluating the nature and extent of contamination in a solvent used for cleaning mechanical parts, said comparator comprising opaque frame, and array of viewing apertures formed in said frame, each of said apertures being covered by a translucent viewing panel, with certain of said viewing panels comprising a first array having a graduated sequence of predetermined colors and optical densities, each indicative of a given level of soluble liquid contamination, and the remainder of said viewing panels comprising a second array having a graduated sequence of predetermined optical densities, each indicative of a given level of contamination by suspended particles, said arrays being arranged so as to facilitate comparison between both the color and optical density of a sample of solvent received in a transparent tube, and both the color and optical density of a particular viewing panel when said viewing panel and said sample-containing tube are alternately illuminated by an intense but diffused light source.

2. A visual comparator as defined in claim 1 wherein said opaque frame is made from a stiff but resilient paper material.

3. A visual comparator as defined in claim 1 wherein said comparator includes, in addition to said opaque frame, a pair of folding flaps adapted, in their closed positions, to provide protective cover elements for said viewing panels in said opaque frame.

4. A visual comparator as defined in claim 3 wherein at least one of said flaps contains instructional guideline information regarding the use of said comparator.

5. A visual comparator as defined in claim 1 wherein said translucent viewing panels are made from a photographic film.

6. A visual comparator as defined in claim 1 wherein said first array of viewing panels comprises at least five viewing panels.

7. A visual comparator as defined in claim 1 wherein said second array of viewing panels comprises at least four viewing panels.

8. A method of determining the condition of a mass of previously used cleaning solvent from time to time during use thereof to maximize the extent to which said solvent may be used without recycling, said method comprising utilizing a mass of cleaning solvent to clean mechanical parts for a given period of time, placing a specimen of the solvent thus used into a transparent container, positioning a light source behind a visual comparator having plural viewing apertures therein with said viewing apertures forming an array arranged in a graduated sequence, each aperture including a translucent viewing panel having a color and optical density indicative of the nature and extent of solvent contamination by both soluble materials and dispersed particulates, positioning said solvent specimen so as to facilitate comparing selected ones of said viewing panels and said specimen of solvent to determine whether said solvent requires clarification by reason of the concentration of particulates appearing to be present therein, treating said mass of solvent when indicated with an organic clarifying agent that is miscible with said solvent, thereafter continuing to use said mass of solvent for cleaning, periodically repeating said steps of comparing said solvent specimen with said viewing panels and adding clarifying agent where indicated until a end point particulate concentration is reached which cannot be diminished by the addition of said clarifying agent, or until comparison of said specimen with a viewing panel indicates an undesirably high degree of soluble contaminants, whereafter said solvent may not be clarified and used successfully, and thereafter recycling said solvent to remove particulate materials and soluble contaminants.

9. A method as defined in claim 8 wherein said clarifying agent is selected from the class consisting of C-9 and lower diols and glycol ethers.

10. A method as defined in claim 8 wherein said clarifying agent includes 2-ethyl 1-3-hexane diol.

11. A method as defined in claim 8 wherein said clarifying agent includes diethylene glycol mono-butyl ether.

12. A method as defined in claim 8 wherein said clarifying agent includes propylene glycol n-butyl ether.

* * * * *